United States Patent
Dieterle et al.

(10) Patent No.: US 7,277,807 B2
(45) Date of Patent: Oct. 2, 2007

(54) METHOD FOR PROCESSING A SET OF SPECTRA, PARTICULARLY NMR SPECTRA

(75) Inventors: Frank Dieterle, Basel (CH); Alfred Ross, Lörrach (DE); Goetz Schlotterbeck, Efringen-Kirchen (DE); Hans Senn, Windisch (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/386,442

(22) Filed: Mar. 22, 2006

(65) Prior Publication Data

US 2006/0217926 A1 Sep. 28, 2006

(30) Foreign Application Priority Data

Mar. 24, 2005 (EP) .................................. 05006476

(51) Int. Cl.
*G01R 23/16* (2006.01)
*G01N 24/00* (2006.01)
(52) U.S. Cl. ........................................ 702/76; 436/173
(58) Field of Classification Search .................. 702/76, 702/179, 75; 324/307–312; 436/173, 174
See application file for complete search history.

(56) References Cited

U.S. PATENT DOCUMENTS

| | | | | |
|---|---|---|---|---|
| 5,027,072 | A * | 6/1991 | Rinaldi | 324/312 |
| 5,592,402 | A | 1/1997 | Beebe et al. | |
| 5,939,884 | A * | 8/1999 | Goldfarb et al. | 324/322 |
| 6,504,368 | B2 * | 1/2003 | Ross et al. | 324/307 |
| 6,831,459 | B2 * | 12/2004 | Szyperski et al. | 324/309 |
| 7,009,394 | B2 * | 3/2006 | Ross | 324/307 |
| 7,076,383 | B2 * | 7/2006 | Schafer et al. | 702/76 |
| 2003/0111596 | A1 * | 6/2003 | Becker et al. | 250/282 |

OTHER PUBLICATIONS

Ross et al., Automation of Measurements and Data Evaluation in Biomolecular NMR Screening, Jun. 11, 2001, DDT vol. 6, No. 11, pp. 583-593.*
Griffiths, L., Towards the Automatic Analysis of H NMR Spectra, 2000, Magnetic Resonance in Chemistry, vol. 38, pp. 444-451.*
Egan W J et al.: "Outlier detection in multivariate . . . " vol. 70, No. 11, Jun. 1, 1998 pp. 2372-2379 XP002366907.
Lenz E et al.: "Metabonomics, dietary influences and cultural differences . . . " vol. 36 (2004) pp. 841-849 XP002366908.
Romano R et al.: "A new algorithm for NMR spectral normalization", vol. 138 (1999) pp. 115-122 XP002366909.

* cited by examiner

*Primary Examiner*—Donald E. McElheny, Jr.
*Assistant Examiner*—Toan M. Le
(74) *Attorney, Agent, or Firm*—Cohen Pontani Lieberman & Pavane LLP

(57) ABSTRACT

A method for processing a set of spectra, particularly NMR spectra, by selecting a principle spectral range, recording a plurality of principle spectra in the principal spectral range, obtaining a reference principal spectrum in the principal spectral range, carrying out, for each one of the principal spectra, a bin-wise division of the principal spectrum by the reference principal spectrum to obtain a corresponding set of spectral quotients; calculating, for at least one of the principal spectra, an associated set of statistical measures derived from the corresponding set of spectral quotients, and carrying out, for at least one of the sets of statistical measures, an outlier detection test.

19 Claims, 11 Drawing Sheets

METHOD FOR PROCESSING A SET OF SPECTRA, PARTICULARLY NMR SPECTRA

TECHNICAL FIELD OF THE INVENTION

The present invention relates to a method for processing a set of spectra, particularly NMR spectra, according to the preamble of claim 1.

BACKGROUND OF THE INVENTION

The analysis and comparison of mixtures is an important task of analytical chemistry, especially in environmental sciences, biology, food industry and process chemistry. For example in the field of metabonomics, biofluids of animals and humans are characterized by the spectra obtained with established spectral methods such as Liquid Chromatography/Mass Spectroscopy (LC-MS) or Nuclear Magnetic Resonance (NMR) spectroscopy. It is often necessary to analyze and compare a whole set of spectra, e.g. a plurality of individual spectra obtained from a set of samples. To separate effects related to changes of overall concentrations of samples (changes of all analytes of samples, e.g. by dilution of samples) from effects influencing the compositions of samples (relative concentrations of components in the mixtures), it is necessary to to use so-called normalization procedures. Normalization is also needed if the data of various samples were taken under different experimental conditions.

Up to now, it was a common procedure in metabonomics studies—e.g. with urine samples—to normalize the signal in a given NMR spectrum so as to obtain a constant overall integral of said spectrum. This means that every NMR spectrum in a set of spectra is scaled to the same predefined area under the curve. The underlying assumption is that the integral of each spectrum is mainly a function of overall urine concentration. Variations of the concentration of individual analytes due to metabonomic responses are assumed to be relatively small in contrast to variations of overall urine concentrations, the latter of which affect the entire spectrum and said predefined area of the spectrum respectively. However, animals in metabonomic studies can excrete extreme amounts of substances like sugars, which may dominate the spectrum and consequently will substantially influence the normalization. In addition, drug related compounds that are excreted with urine may also influence the normalization through the integral of their corresponding peaks and may thus contribute significantly to the total integral of a spectrum. The same type of problem arises in other analytical applications comparing mixtures, where the appearance of an unknown contaminant with a comparatively high concentration might significantly affect the total integral of a spectrum or said predefined area of the spectrum.

A method for quantification of chemical mixtures components studied by mass spectroscopy is disclosed in US 2003/0111596 A1. As described particularly in Paragraph 0040 of said document, the known method relies on:
a) obtaining a set of sample spectra from a plurality of chemical samples, each spectrum comprising peaks having peak intensities;
b) selecting a reference spectrum;
c) for any of said sample spectra to be normalized, computing intensity ratios between the sample spectrum and the reference spectrum for all peaks or for a fraction of the total number of peaks; and
d) mutiplying the sample spectrum with a normalization factor that is computed from said intensity ratios.

The above method relies on the fact that under many practical circumstances the majority of said intensity ratios will be substantially equal, representing components whose concentrations do not vary between the sample and reference spectra. The normalization factor may then be computed from said intensity ratios using a non-parametric measure. Preferably, the normalization factor is chosen to be the median of said intensity ratios.

As further pointed out in Paragraph 0031 of US 2003/0111596 A1, the known normalization method is applicable to any type of spectroscopy or spectrometry yielding spectra containing signals (or peaks) whose intensities or areas are proportional to component concentrations. In particular, it should thus be applicable to NMR spectroscopy.

However, the method disclosed in US 2003/0111596 A1 does not address the problem of identifying and eliminating so-called "outliers", which may notably be individual signals originating from or distorted by artifacts, but also entire spectra with some type of deviation, e.g. due to technical failure during acquisition. This problem is particularly important in quantitative analysis of large numbers of spectra, such as in metabonomics studies.

SUMMARY OF THE INVENTION

It is the principal object of the present invention to overcome the limitations and disadvantages of currently known methods for quantitative processing of spectra, particularly NMR spectra.

The foregoing and further objects are achieved by the method of the present invention.

According to claim 1, there is provided a method for processing a set of spectra, particularly NMR spectra, comprising the steps of:
a) selecting a principal spectral range;
b) recording a plurality of principal spectra in said principal spectral range;
c) obtaining a reference principal spectrum in said principal spectral range;
d) carrying out, for each one of said principal spectra, a bin-wise division of the principal spectrum by said reference principal spectrum to obtain a corresponding set of spectral quotients;
e) calculating, for at least one of said principal spectra, an associated set of statistical measures derived from the corresponding set of spectral quotients; and
f) carrying out, for at least one of said sets of statistical measures, an outlier detection test.

While the method of the present invention is useful for and exemplified by applications in NMR spectroscopy, it may also be applied to other types of spectroscopy yielding spectra containing signals (or peaks) whose intensities or areas are proportional to component concentrations, such as mass spectroscopy or various types of optical spectroscopy.

In the present context, the term "spectral range" shall be used—as the case may be—for a single region in a spectrum or for a plurality of disjoint regions. In particular, a spectral range of interest may be a plurality of spectral regions each containing a certain number of signal peaks. The attribute "principal" shall be used here in contradistinction to "auxiliary" as adopted for certain embodiments of this invention. In particular, "principal spectral range" will be used to denote a spectral range that contains one or more relevant signal peaks of a certain sample. It should be noted that spectra are typically acquired in an overall spectral range that contains said principal spectral range and—if applicable—an auxiliary spectral range; moreover, the overall spectral range may contain further spectral ranges that are not used for further analysis. For example, $^1$H NMR spectra in metabonomics studies are often recorded in an overall spectral range from −8 to +14 ppm, wherefrom the principal spectral range is selected as consisiting of two regions from 1 to 4.5 ppm and from 6 to 9.5 ppm, respectively.

In essentially all spectroscopy applications nowadays, one obtains spectral data in digital form. For example, a one-dimensional NMR spectrum will generally be available as a sequence of intensity values, each of which is associated to a particular spectral channel or "bin". Thereby, the term "bin" can also refer to a sum of intensity values. Accordingly, a "bin-wise division" of a first spectrum by a second spectrum shall be understood here as taking the intensity value in a certain bin of the first spectrum, dividing it by the intensity value in the same bin of the second spectrum, assigning the division result to the same bin of a resulting set of spectral quotients and repeating this procedure for all the bins in the spectral range of interest. It will be understood that if spectra were available in non-digital, i.e. analog form, one could nonetheless carry out a bin-wise division in the sense of the present invention. This would simply necessitate that any analog spectra are first converted to a digital form by means of a suitable binning procedure as known in the art of signal processing.

The term "statistical measure" shall refer to any number whose size indicates the magnitude of some quantity of interest, e.g. the strength of a relationship, the amount of variation, the size of a difference or the shape of a distribution. Examples include means, variances, correlation coefficients and many others.

The term "outlier" shall refer to any entity—particularly a signal peak, a spectrum or part thereof comprising several signal peaks, or even an entire set of spectra—whose score on a given variable deviates substantially from a predefined numerical range. Accordingly, an "outlier detection test" shall be understood as any type of procedure aimed at determining whether or not a given entity should be considered an outlier in respect of a given test criterion.

The method according to this invention may readily be implemented in automatic processing of spectral data. As will be exemplified further below, the actual type of outlier detection tests to be applied in the processing sets of NMR spectra may be adapted to any application of interest. The method may be embedded in an overall procedure wherein, for example, a spectrum identified as an outlier would be discarded from further analysis.

Advantageous embodiments are defined in the dependent claims.

In general, the set of statistical measures corresponding to a principal spectrum will be chosen so as to adequately describe the position and shape of the distribution of spectral quotients. Accordingly, it is advantageous to use at least one position measure and one width measure. In the embodiment according to claim 2, the set of statistical measures corresponding to a principal spectrum comprises the median of its spectral quotients and an interquartile difference obtained by subtracting the first quartile of its spectral quotients from the third quartile of its spectral quotients. These statistical measures are known to be comparatively robust. Nevertheless, other choices are possible: one may use the mode or the mean as a position measure and one may use the difference between other quantiles as a width measure.

In the embodiment according to claim 3, said outlier detection test comprises determining whether said interquartile difference exceeds a predefined threshold width. Such a large interquartile difference is indicative of a broad distribution of spectral quotients and thus means that the intensity across the instant spectrum relative to the reference spectrum shows substantial variation and not just a simple scaling behavior. According to claim 4, the threshold width is determined from the distribution of said interquartile differences taken over the entire set of principal spectra. In other words, one first obtains an overall impression of the interquartile differences found in all the spectra of a given set in order to then define a threshold width for the outlier detection test.

In the embodiment according to claim 5, said outlier detection test comprises determining whether said median of spectral quotients differs from a constant by more than a predefined threshold quotient deviation. Such a large deviation is indicative of a deviation in overall intensity of the instant spectrum relative to a given standard value. According to claim 6, the threshold quotient deviation is determined from the distribution of said median of spectral quotients taken over the entire set of principal spectra. In other words, one first obtains an overall impression of the median of spectral quotients found in all the spectra of a given set in order to then define a threshold deviation for the outlier detection test.

Another advantageous embodiment is defined in claim 7, according to which the method further comprises the steps of:
a) selecting an auxiliary spectral range that does not overlap with said principal spectral range,
b) recording, with each one of said principal spectra in said principal spectral range, an associated auxiliary spectrum in said auxiliary spectral range;
c) obtaining a reference auxiliary spectrum in said auxiliary spectral range;
d) carrying out, for each one of said auxiliary spectra, a bin-wise division of the auxiliary spectrum by said reference auxiliary spectrum to obtain a corresponding set of auxiliary spectral quotients; and
e) calculating, for each one of said auxiliary spectra, an associated set of statistical measures derived from the corresponding set of auxiliary spectral quotients;

and wherein said outlier detection test comprises comparing statistical measures of a principal spectrum and of an associated auxiliary spectrum. In particular, the auxiliary spectral range may be chosen in a region where one expects problems or artifacts to be more likely, whereas the principal spectral range is chosen in a region known to be less susceptible to problems and artifacts. The auxiliary spectrum may then be used as a sort of diagnostic tool. As mentioned earlier, any of the spectral ranges discussed here may consist of a single spectral region or it may consist of two or even more disjoint spectral regions.

Yet a further advantageous embodiment is defined in claim 8, according to which step 1e) is carried out for each one of the principal spectra so as to obtain a complete set of statistical measures from which is derived a set of global statistical measures, and wherein said outlier detection test is carried out for said set of global statistical measures. In other words, the outlier detection test is carried out making use of statistical information derived from an entire set of spectra, which should make the test as objective as possible. According to claim 9, said set of global statistical measures comprises:
a) the median of the complete set of said interquartile differences; and
b) the interquartile difference of the complete set of said interquartile differences.

However, other choices of statistical measures are possible.

In principle, it is possible to carry out the methods discussed so far by using spectral data uncorrected for intensity. In most applications, however, it will be preferable to apply the method defined in claim 10, according to which each one of said principal spectra and—if applicable—each one of said auxiliary spectra is subjected to a normalization procedure before carrying out the bin-wise division. Advantageously, this is done according to the embodiment of claim 11, wherein said normalization procedure for any one of said principal or auxiliary spectra comprises the steps of:

a) applying to said spectrum a pre-processing to obtain a pre-processed spectrum;
b) calculating an integrated intensity of said pre-processed spectrum; and
c) multiplying said pre-processed spectrum by a normalization factor that is proportional to the inverse of said integrated intensity.

The type of pre-processing procedure will generally depend on the type and quality of spectra. It may include a smoothing or filtering procedure in case of noisy data; in particular it may include a baseline correction or subtraction procedure, which will be appropriate for spectra with a substantially flat or slowly varying background component. In particular for NMR spectra, the pre-processing may include zero-filling, phasing, application of a window function and linear prediction. Further pre-processing steps may include integration and derivation of spectra.

In practice, the normalization factor contains a proportionality constant that ensures that any normalized spectrum will have a predefined integrated intensity such as 1 or 100 or any other convenient value.

There are several choices for the reference spectrum to be taken for processing a set of spectra. For example, it could be a calculated reference spectrum, a reference spectrum taken from a database or a theoretical spectrum. According to claim 12, the reference principal or auxiliary spectrum is obtained as the median of a plurality of blank or control spectra recorded in the corresponding principal or auxiliary spectral range, respectively. Alternatively, according to claim 13 the reference principal or auxiliary spectrum may be obtained from a subset of said principal or auxiliary spectra. This subset could consist of just a single spectrum or it could consist of a plurality of spectra; in the latter case, the reference spectrum could be obtained e.g. as the median or the mean of said plurality of spectra. Finally, it should be noted that the term "subset" should be understood as including the case where the subset is identical to the entire set of spectra.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein.

DETAILED DESCRIPTION OF THE INVENTION

Figure 1:
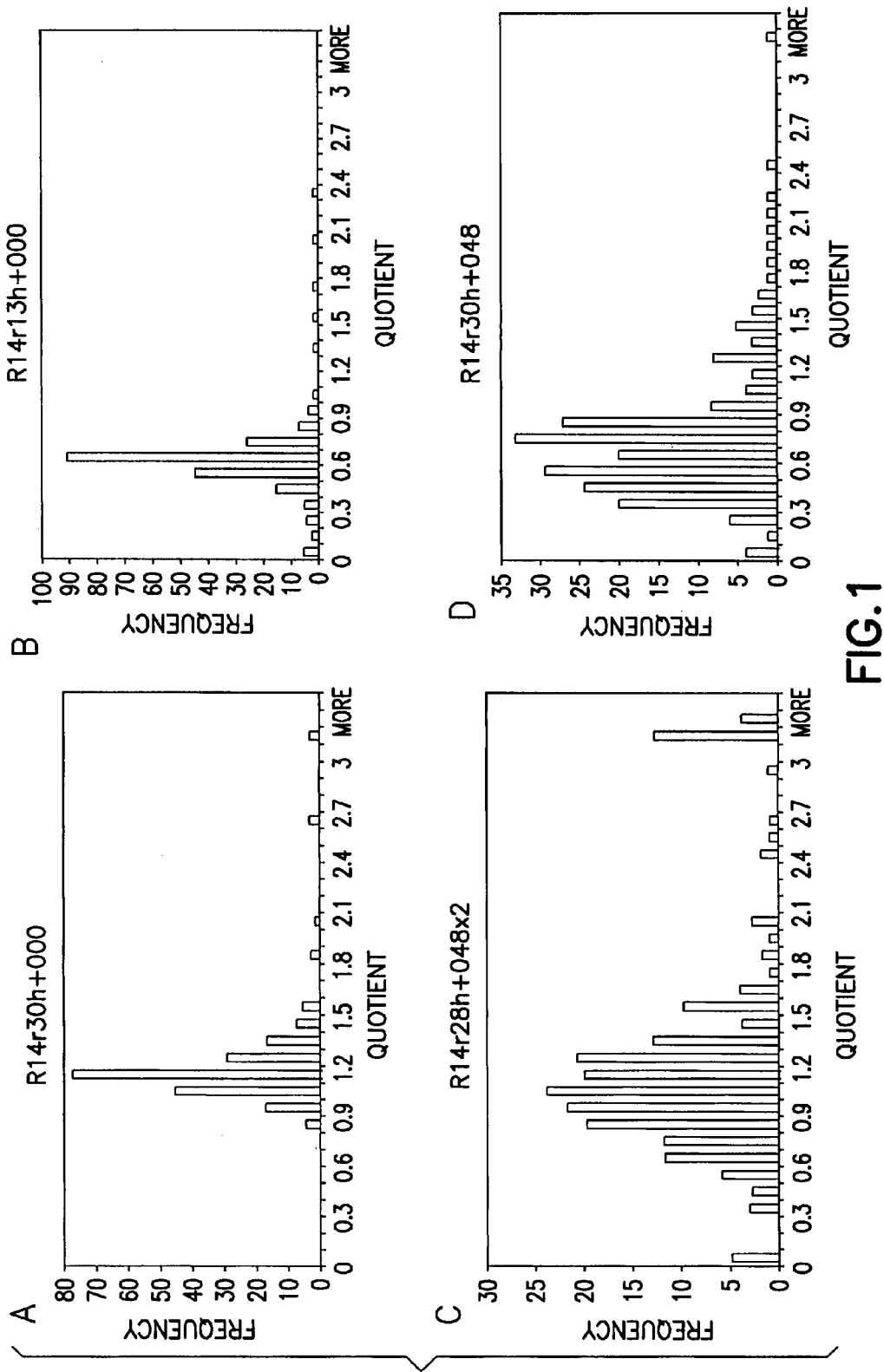
FIG. 1: shows, for four samples of a metabonomic study in respect of 208 variables (bins), the distributions of spectral quotients with respect to a reference sample of the same study.

The following section describe the background and techniques needed to apply the method of this invention, including most notably, a discussion of various normalization approaches. While these methods could be applied to various types of spectroscopy, the following discussion will be exemplified by NMR spectra, particularly $^1$H-NMR spectra.

In general, an NMR spectrum of interest would be described in terms of its intensity I as a function of chemical shift δ. However, it will be assumed that spectra are available in bin-wise digitized form and thus will be written as I(i), where i is a running index denoting a given bin. The "signal" I(i) may be understood as the result obtained by integrating the signal across the spectral ranged spanned by the i-th bin. In most cases, the binning will be equidistant.

1. Normalization of Spectra

This section describes three commonly used techniques for normalization of spectra, namely: integral normalization, creatinine normalization and vector length normalization. Subsequently, quotient normalization is introduced. The first three normalization techniques can be expressed as specific cases of the general equation:

$$I(i) = \frac{I^{old}(i)}{\sum_k \int_{j_k^l}^{j_k^u} (I(x))^n \, dx} \quad (1)$$

Herein, $I^{old}(i)$ and $I(i)$ are the spectral intensities before and after normalization, respectively, k is an index of the spectral region used for normalization, $j_k^l$ and $j_k^u$ are the lower and upper borders, respectively, of the spectral region k for which the power n of intensity $I(x)$ is integrated.

1.1 Integral Normalization

With integral normalization it is assumed that the integrals of spectra are mainly a function of the concentrations of samples. A linear concentration series of urine should thus result in a linear series of integrals of the corresponding spectra. The influence of changes of individual concentrations of single analytes is assumed to be small as compared to changes of the overall concentration of urine.

The integral normalization procedure divides each spectrum by the integral of the spectrum or by a part thereof. Thus, the power n in general equation (1) is taken as 1. In the field of NMR measurements for metabonomics, it is a common procedure to select a spectral range that actually comprises two spectral regions, namely the one between 9.98 and 5.98 ppm and the one between 4.50 and 0.22 ppm. Moreover, it is customary to further multiply each spectrum by a factor of 100, thus ending up with a total integral of 100 for each spectrum.

A problem with integral normalization is the interdependency of signals. Obviously, any single strong signal will cause the normalization procedure to scale down all the other signals, thus leading to an apparent reduction of the concentration of all analytes in the mixture.

1.2 Creatinine Normalization

For the investigation of urine of humans and animals, it is a common procedure to normalize concentrations of analytes and spectra by means of the concentration of creatinine. The underlying assumption is a constant excretion of creatinine into urine. Thus, creatinine is taken as indicator of the concentration of urine. Two possibilities exist for normalization: The level of creatinine can be determined externally by clinical chemical procedures or internally by integration of creatinine related signals in the NMR spectrum. This latter method can be expressed as a special case of integral normalization. In terms of the general equation (1), two integration regions (corresponding to creatinine peaks at 3.04 and 4.05 ppm) and a power of 1 are used.

Yet, the practical application of the creatinine normalization faces technical and biological difficulties. If the concentration of creatinine is determined by the NMR spectrum, metabolites with overlapping peaks can interfere with the determination of the concentration of creatinine (e.g. creatine at 3.04 ppm). A second difficulty for the determination of creatinine using $^1$H NMR spectra is that the chemical shift of creatinine near 4.05 ppm depends on the pH-value of the sample. Therefore, either a peak picking algorithm or a rather broad range of the spectrum has to be used for the normalization.

Biological challenges for the creatinine normalization are changes of creatinine concentration due to metabonomic responses, as found in several studies. At the time of normalization, a possible increase of the creatinine level due to metabonomic responses is usually not yet known. Therefore, creatinine-based normalization is not of general use in metabonomics and will not be discussed further herein. Nevertheless, the creatinine peaks will be used to investigate the correlation between creatinine level and the normalization factors obtained with various methods for a subset of spectra where a strict correlation between concentration level and creatinine is known to hold.

1.3 Vector Length Normalization

A normalization technique applied in many scientific fields is based on looking at spectra as vectors. In other words, the sequence of intensity values $I(i)$ is taken to represents the components of an associated vector. It is further assumed that the length of such a vector is determined by the concentration of the corresponding sample; the composition of a sample will thus determine the direction of the vector. Accordingly, the adjustment of different concentrations is performed by setting the lengths of vectors to 1. Note that this is equivalent to setting the power n of general equation (1) to 2. Like with integral normalization, all the peaks in a spectrum influence each other due to the calculation of a common vector length.

1.4 Quotient Normalization

Quotient normalization rests on the assumption that changes in concentrations of single analytes only influence parts of a spectrum, whereas changes of overall concentrations of samples influence the complete spectrum. Other than with integral normalization, one calculates the most probable quotient between a given spectrum and a reference spectrum, which quotient is then used to obtain a normalization or scaling factor.

For this procedure, a bin-wise division of the spectrum and a previously selected reference spectrum is carried out to obtain a set of spectral quotients. It will be understood that this procedure is made in some appropriately selected spectral range. Ideally, the distribution of spectral quotients will be narrow, in the limit of two identical samples with different concentrations, the respective spectral quotients will differ according to the concentration ratio.

The most probable spectral quotient, which may be determined by several methods, represents the ratio of concentrations between the sample and the reference. Panel A of FIG. 1 shows the distribution of spectral quotients between sample R14r30h+000 of a metabonomic study and of a reference sample of the same study. This sample is found to be slightly more concentrated than the reference sample, as the most probable quotient (approximated as the maximum of the histogram) is located around 1.1. On the other hand, panel B of FIG. 1 shows the result for a comparatively diluted sample of the same study, which is found to have a most probable quotient of about 0.6 compared to the reference sample.

If, however, the concentrations of single analytes change due to metabonomic changes, only certain parts of the corresponding spectrum will be affected. The result is a wider distribution of spectral quotients. Panel C of FIG. 1 shows distribution of spectral quotients of a sample with extreme intensity variations across its spectrum due to a strong metabonomic change. This results in a broad distribution due to parts of the spectrum with enhanced and reduced intensity, respectively. Extreme spectral quotients exceeding a value of 10 are caused by an extreme amount of glucose excreted in this specific sample. Nevertheless, as the total concentration of urine is essentially unchanged, the most probable spectral quotient is still close to 1. In contrast, panel D of FIG. 1 shows the histogram of a sample with both effects, i.e. specific changes due to strong metabonomic responses and also a dilution of the sample due to enhanced urine excretion. Accordingly, the distribution of spectral quotients is broadened and shifted to lower values.

An important aspect of quotient normalization is the determination of the most probable spectral quotient, since this will be used as scaling factor. In the previous paragraph, the most probable spectral quotient was determined by taking the maximum of the histogram of spectral quotients. However, the exact position of the maximum of a distribution depends on the binning width. Therefore, the schematic analysis of histograms presented so far cannot be regarded as a robust and general method to define the optimum quotient. Using a too rough binning leads to a rather large quantization error (for example, the difference between a quotient of 1 and 1.1 corresponds to a quantization error of 10%), whereas a too fine binning leads to histograms without a clear maximum, as shown in panel D of FIG. 1. A practical approach approximates the most probable quotient by using the median of quotients. The advantage of the median method is that no discrete grouping (binning) of the quotients for a histogram is needed, which is arbitrary. The median method allows a very fine adjustment of spectra without the danger of extreme quotients significantly influencing the adjustment.

The reference spectrum used for calculating the spectral quotients can be a single spectrum obtained from a "golden" reference sample. Alternatively, a median or average spectrum of several spectra can be used. The influence of the type of reference spectrum is discussed in section 4.1.3. It is found that the reference spectrum should be as representative as possible. Therefore it is recommended to calculate the reference spectrum as the median spectrum of a plurality of non-dosed samples (control samples and pre-dosed samples).

The quotient normalization can be preceded by an integral normalization (usually to an integral of 100). This simplifies comparing studies measured with different spectrometers resulting in different absolute scale values of the spectra. Typically, the method of quotient normalization will thus involve the following steps:

A1. Perform an integral normalization (typically a constant integral of 100 is used).
A2. Choose or calculate a reference spectrum (best approach: calculate median spectrum of non-dosed samples).
A3. Carry out a bin-wise division of the sample spectrum by the reference spectrum to obtain a corresponding set of spectral quotients.
A4. Calculate the median of spectral quotients.
A5. Re-scale the sample spectrum by multiplying it with the inverse of said median.

As remarked earlier, step A1 is optional, but will be advantageous in most cases.

2. Outlier Detection 2.1 Background

The methodology underlying quotient normalization was further developed to provide for an automated detection of outliers. During automated sample preparation, measurement and data processing, many things can happen that influence the quality of data obtained. For example, technical problems like an incorrect gain of the detector, insufficient suppression of the water resonance, spikes at both borders of the spectrum or problems during processing of the data like incorrect referencing, wrong baseline correction and non-appropriate phasing all can occur when measuring NMR spectra. In addition, the absence or a too low concentration of urine in samples should be automatically detected.

In metabonomic studies (or e.g. NMR spectra obtained for quality control of production batches) most analytes have stable relative concentration, and thus the majority of signal peaks will behave accordingly. In contrast, corrupted spectra usually have a different global shape, which results in an unusually wide distribution of spectral quotients as compared to intact spectra. This feature can be used for the detection of outliers and for the definition of measures to judge overall quality of measurements performed on chemically similar samples.

2.2 Outlier Detection Procedure

A procedure for an off-line detection of outliers (here "offline" means that the detection is performed after completion of the experiment) involves the following steps:

B1. Perform an integral normalization for the entire set of spectra from a study.
B2. Calculate a reference spectrum (median spectrum of non-dosed samples).
B3. Carry out a bin-wise division of the sample spectrum by the reference spectrum to obtain a corresponding set of spectral quotients.
B4. Calculate, for each one of the spectra, the median of spectral quotients (henceforth denoted as m) and the difference between the first and the third quartile of spectral quotients (henceforth called "interquartile difference" and denoted as d). The median m may be used for quotient normalization of the instant spectrum (actually by using the inverse of m as a scaling factor).
B5. Carry out an outlier detection test. For example, the interquartile difference d is a measure of how the shape of the instant spectrum differs from that of the reference spectrum. Accordingly, a criterion for outliers would be a value of d that exceeds a preselected threshold width. Further outlier tests are discussed hereinbelow.

As remarked earlier, step B1 is optional, but will be advantageous in most cases. Typically, step B4 is performed for all the spectra of a measurement series, but this is no stringent requirement, i.e. one may also carry out step B4 for only a subset of spectra.

The modifications for an online version of the above procedure, which can be used for real time controlling of spectral detection and processing, are rather moderate as only step B2 needs to be modified. A practical approach is measuring a reference set of pre-dosed samples or control samples at the beginning of a series of measurements. A median reference spectrum is then calculated on the basis of this set of spectra. Using the robust median allows the presence of a certain percentage of corrupted data to be present in the reference set. All the following steps of the above procedure are based on a spectrum per spectrum basis and thus are well suited for an on-line version of the algorithm.

2.3 Finding Outliers and Damaged Spectra

Most outliers due to technical failure during acquisition will result in spectra with totally different shapes (for example, lines and curves of arbitrary shape instead of real spectra). Thereby, a different shape results in a very broad distribution of the spectral quotients of the corresponding spectrum. The consequence is an atypically large interquartile difference d. Although arbitrary, a fixed value for d of 1 has proven to be a reasonable threshold width for NMR spectra of metabonomic studies. Values of d exceeding this threshold width are typical indications for damaged spectra or problems affecting large parts of spectra. Instead of using a fixed and rather arbitrary threshold for d, one can use the distribution of d with the median md of d and the interquartile difference dd of d. A threshold for d can then be set according to $d_{critical}$=md+n·dd wherein n is a parameter for adjusting the detection of outliers in respect to sensitivity and specificity.

A second type of outliers can be detected by considering the median of spectral quotients m. If the interquartile difference d does not indicate an outlier but the median of spectral quotients m significantly deviates from 1, it is likely that a spectrum with strong deviations in only a small spectral ranged "fooled" the integral normalization (step B1). This can be due to a technical problem affecting only a small part of the spectrum (e.g. spikes or poor water peak suppression) or due to animals with extraordinary metabonomic responses. Although no discrimination between extraordinary animals and technical problems can be made, the outlier detection indicates the samples that will have to be further investigated. A rule of thumb for the detection of outliers concerning m is a deviation of ±0.15 from the ideal value of 1. Again, instead of using these hard thresholds, one may use study specific thresholds like the median mm of medians m and the interquartile difference dm of medians m. Thereby, critical thresholds for the medians can be set according to: $m_{critical}$=mm±n·dm with the parameter n determining the sensitivity and specificity.

2.4 Finding Specific Technical Problems

If a region within a spectrum is known that is typically affected by a specific technical problem, this region can be selected as an auxiliary spectral range. The spectral quotients within this auxiliary range can then be compared with the spectral quotients in the unaffected spectral region(s) of the spectrum, henceforth called "principal spectral range", in order to detect specific problems. The procedure thus involves the following steps:

C1. Select a principal spectral range and an auxiliary spectral range that does not overlap with the principal spectral range.
C2. Record a plurality of principal spectra in the principal spectral range and, for each one of said principal spectra, record an associated auxiliary spectrum in the auxiliary spectral range.
C3. Obtain a reference principal spectrum in the principal spectral range and a reference auxiliary spectrum in said auxiliary spectral range.
C4. Carry out, for each one of the principal spectra, a bin-wise division of the principal spectrum by the reference principal spectrum to obtain a corresponding set of spectral quotients; and carry out, for each one of the auxiliary spectra, a bin-wise division of the auxiliary spectrum by the reference auxiliary spectrum to obtain a corresponding set of auxiliary spectral quotients.
C5. Calculate, for at least one of said principal spectra, the median of principal spectral quotients, called mp.
C6. Calculate, for each auxiliary spectrum associated with said principal spectra, the median of auxiliary spectral quotients, called ma.
C7. Calculate the quotient of mp and ma, called qs.
C8. Carry out an outlier detection test by comparing qs with the reference value of 1.

If this quotient substantially deviates from 1, the spectrum in the specific, auxiliary region is substantially different from the rest of the spectrum, which is a strong indication for a specific problem. Again, fixed thresholds or soft thresholds based on the distribution of qs can be used. A typical problem which can be treated in this way is the quality of suppression of water resonances. For that purpose, the specific auxiliary range is selected to contain the spectral regions located next to the water resonances.

2.5 Determining the Quality of a Complete Study

Typically, metabonomic studies are performed by measuring a considerable number of samples. These samples are obtained from "dosed" animals that received a certain drug or substance and from "non-dosed" animals that did not receive said drug or substance. The spectra thus measured will show variations due to inherent inter-animal variations, due to metabonomic responses and due to inter-measurement variations (technical problems . . . ). Among all these variations, the metabonomic responses usually lead to the most localized changes in the spectra. As usually the objective of a metabonomic study is to investigate metabonomic responses, "the quality" of a metabonomic study can be judged by looking for non-localized changes of the shape of spectra, since these are most likely not due to metabonomic responses. An overall quality measure of a study can be obtained if the algorithm introduced in section 2.2 is extended by a further step:

C9. Carry out step C5 (and accordingly step C6) for all the spectra and calculate for each spectrum the interquartile difference d of the quotients and the medians m of the quotients. Then calculate the interquartile difference dm for all medians m of the study. After that calculate the median mm of all medians m of the study. Calculate also the median of all differences d of the study (further called md). Finally calculate the interquartile difference dd of all interquartile differences d of the study.

If a study contains many spectra that significantly differ by shape, the values of md and dd will be rather high. This can either happen due to bad phasing of spectra, very low-concentrated samples, measurement failures and many more. The corresponding impact on the quality of the spectra renders the data analysis of metabonomic responses more challenging.

High values of dm indicate that for several spectra the integral normalization and quotient normalization deviate significantly. If md and dd are high, this deviation is probably due to corrupted spectra. On the other side, high values of dm and simultaneously low values of md and dd indicate that only small parts of several spectra are inconsistent within the study. This means, that several samples are outlying either due to strong metabonomic responses or due to local defects in the spectra such as spikes, contaminations or drug related compounds.

2.6 Graphical Detection of Outliers

Figure 2:
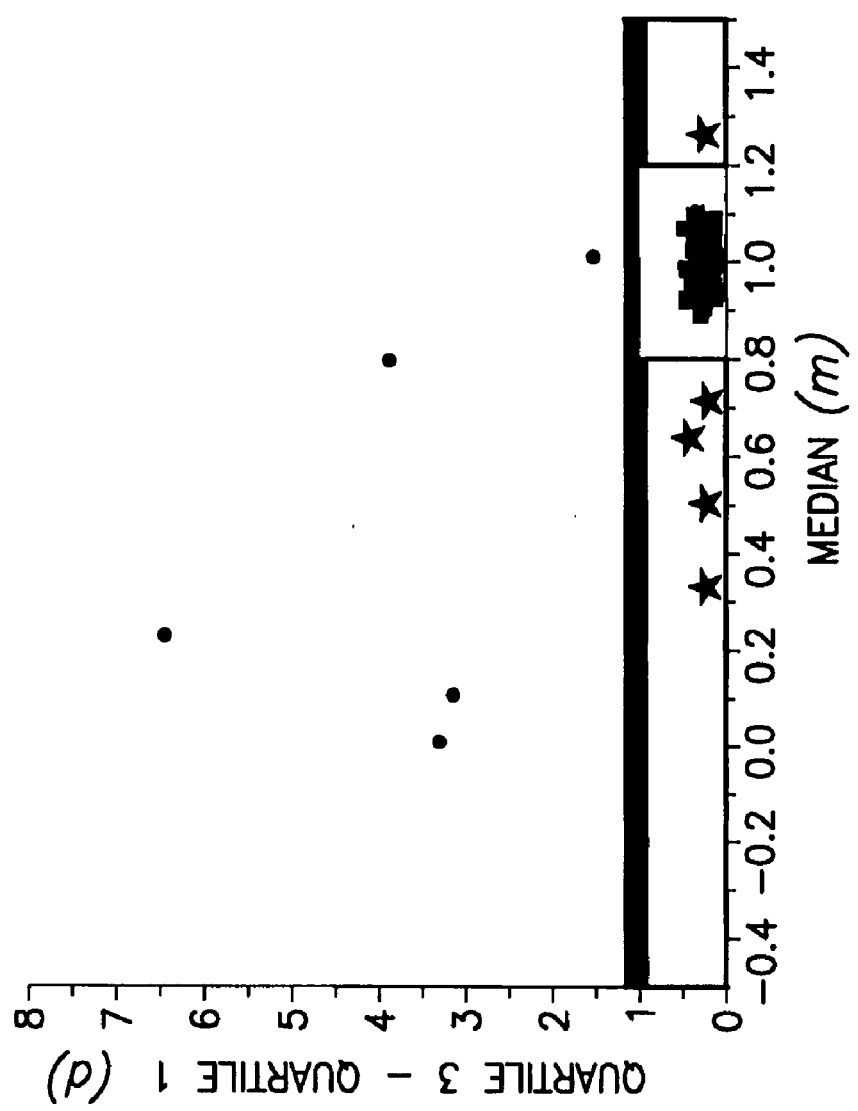
FIG. 2: shows a plot of the difference of quartile 3 minus quartile 1 (called interquartile difference (d)) versus the median (m) for a typical metabonomic study; squares represent spectra that are not outlying, dots represent spectra with broad damages (no sample, bad receiver gain, wrong phasing . . . ) whereas stars represent spectra with local irregularities (spikes, drug related compounds, extraordinary amounts of a metabolite . . . ); fixed thresholds of m (0.8 and 1.2) and of d (1) for the detection of outliers were set.
Figure 3:
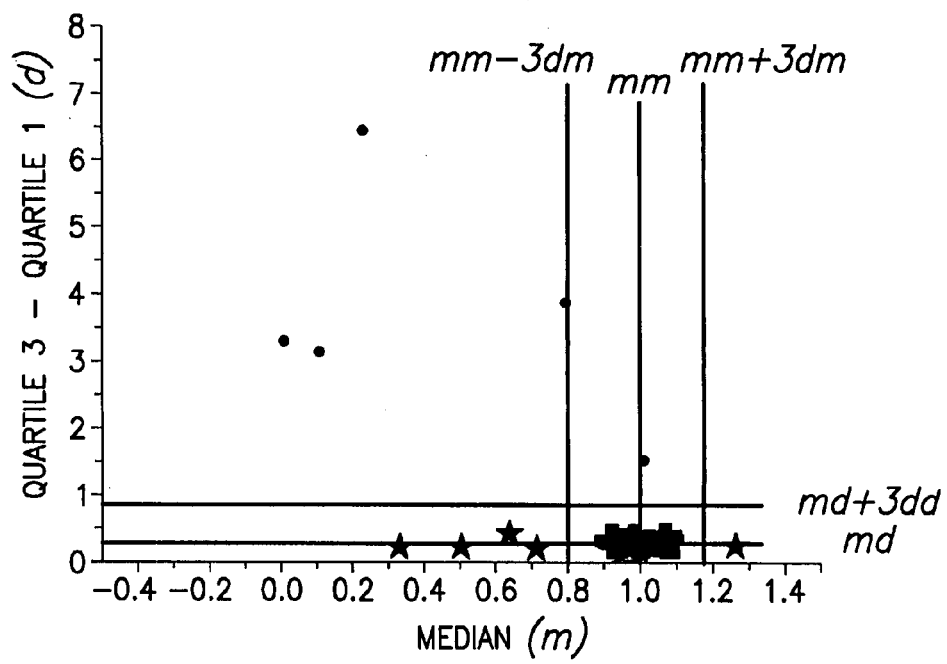
FIG. 3: shows a plot of the data from FIG. 2, but with study specific thresholds instead of fixed absolute thresholds; for all thresholds, n was set to 3.

A graphical tool for the detection of outliers can be obtained by plotting d versus m. Thereby, normal spectra will cluster around m=1 with low values of d. In FIG. 2, these spectra are shown as squares. Spectra with broad damages have values of d higher than a specific threshold, which is typically set to 1. In FIG. 2, these spectra are located above the thick horizontal line and are represented by circles. Spectra which are outlying due to strong metabonomic responses, due to contaminations or due to local damages of the spectra are located below the threshold of d but significantly deviate from m=1. Typically, thresholds for m of 0.80 and 1.20 are set. In FIG. 2, these spectra lie within the two boxes and are represented by stars. Carrying out the same procedure with flexible thresholds using a parameter n=3 leads to the results shown in FIG. 3.

3. Examples

Four types of data sets with different backgrounds are examined here. The first type of data is based on simulations. Thereby a typical urine NMR spectrum of a metabonomic study is systematically varied in order to simulate various effects which can influence normalization. The simulations range from realistic changes up to rather unrealistically extreme changes. A second experimental data set is based on NMR measurements of samples from one metabonomic study. Thereby, normalization procedures are challenged by samples with extreme amounts of metabolites and simultaneously by varying concentrations of urine. For this data set, outliers due to technical issues have been filtered out. The third data set is a collection of more than 4000 NMR measurements of non-dosed rats. These samples only show normal biological and analytical variations, so the data set allows to compare the performance of various normalization procedures under the least demanding conditions. The fourth data set is based on measurements from two metabonomic studies without exclusion of any data. Hence, all kinds of challenges including measurements of blank samples, samples with suboptimal quality and bad spectra due technical issues can be encountered. These data will be used to demonstrate the identification of outliers in realistic situations.

3.1 Simulated Data Sets Used for Normalization

Figure 4:
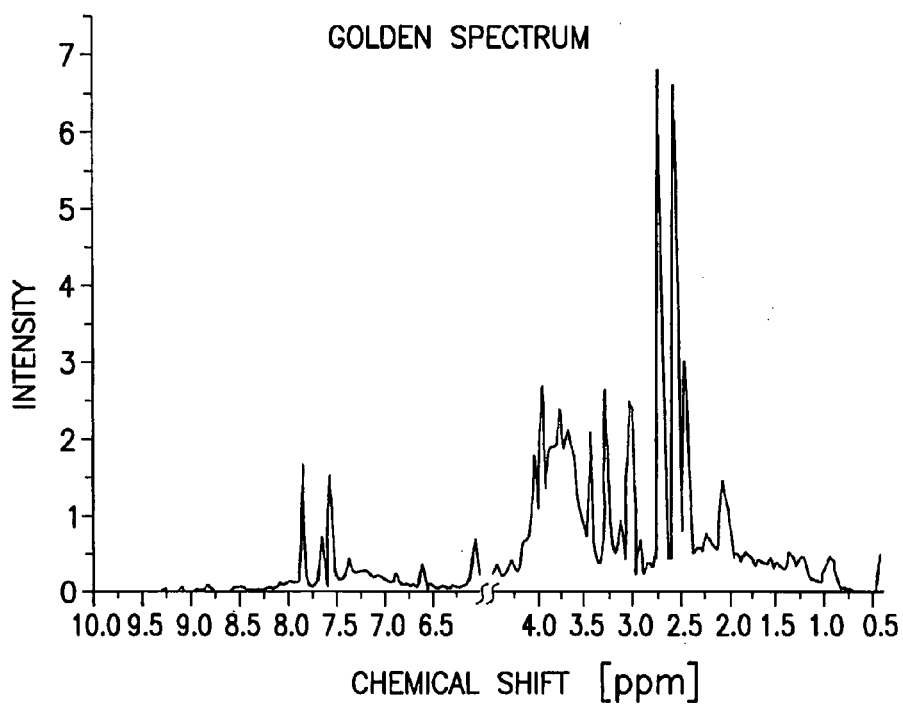
FIG. 4: shows a "Golden" $^1$H NMR spectrum in binned form, used for systematic modifications.

For the simulations of the stability of normalization methods, a "golden spectrum" was systematically varied. The golden spectrum was calculated as median spectrum out of more than 4000 spectra of urine of non-dosed rats. Thus it is believed that the golden spectrum represents a typical spectrum in the area of metabonomics with rat urine. The spectral range (9.96-0.4 ppm) was segmented into integral bins of 0.04 ppm each. The bins of the range between 4.48 and 6 ppm (water and urea) were excluded and the bins of the range where resonances of citrate occur (2.72/2.68 ppm and 2.56/2.52 ppm) were merged into two bins resulting in 201 bins in total. The spectrum was normalized to a total integral of 100. The intensity of the $201^{st}$ bin (0.4 ppm) was artificially set to 0.5. This peak will only be modified to simulate unspecific changes of concentration but not for specific changes. This bin will be used as reference bin to judge the quality of the normalization procedures. The binned golden spectrum is shown in FIG. 4.

Figure 5:
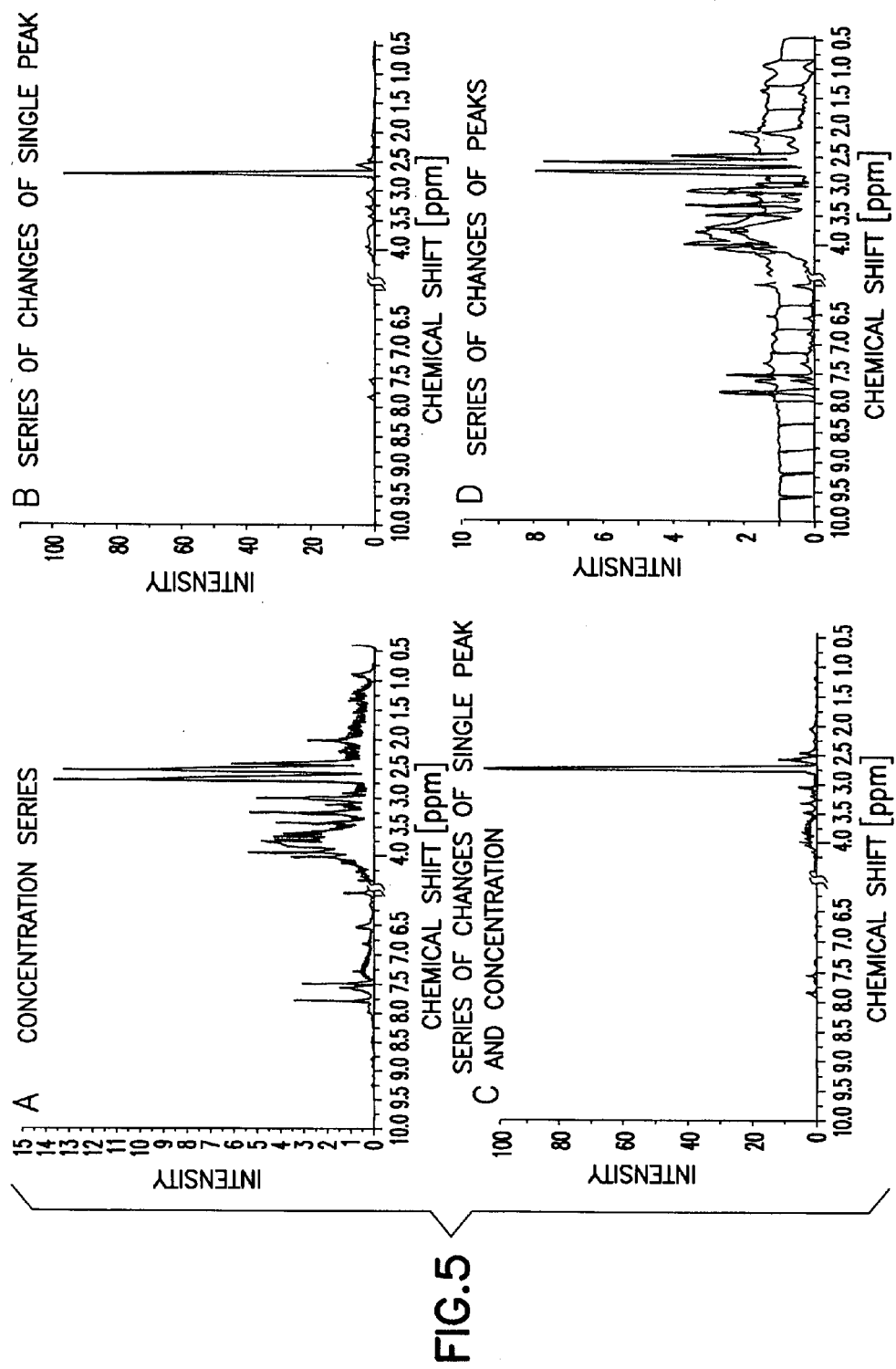
FIG. 5: shows four data sets of series of spectra differing by systematic variations: (A) systematic variation of sample concentration; (B) sytematic variation of a single peak intensity; (C) systematic simultaneous variation of sample concentration and of a single peak intensity; systematic variations of blocks of 10 bins.

The first set of simulated data was generated by systematic variation of unspecific concentrations of samples in steps of 0.1, ending up in a doubled concentration. This was performed by multiplying the intensity of each bin of the golden spectrum with a factor of 1.1, 1.2, 1.3, etc. The series of 11 spectra is shown in panel A of FIG. 5.

The second set of simulated data was generated by systematically varying one single bin. Thereby the peak at 2.7 ppm (one of the two peaks of citrate typically visible in the spectrum) was increased in steps of 10% of the total intensity integral (10 steps in total). The series of 11 spectra is shown in panel B of FIG. 5. It is obvious that this single peak dominates the complete spectrum.

The third set of simulated data represents a combination of the modifications of the first and second simulated data set. Thereby, unspecific concentrations of samples were increased in steps of 10% and simultaneously 10% of the integral intensity of the golden spectrum was added to the peak at 2.7 ppm for each step. The corresponding spectra are shown in panel C of FIG. 5.

For the fourth set of simulated data, blocks of 10 bins were systematically modified simulating specific changes of several peaks. Thereby the intensity of the first 10 bins was increased by 1% of the integral intensity of the golden spectrum for each of the 10 bins. For the second spectrum the first 20 bins were increased. In total, 20 spectra were generated always increasing then more bins from step to step ending up in 300% integral intensity for the last spectrum (compared with the golden spectrum). The systematic variations are visible as blocks of bins in panel D of FIG. 5, whereby only the first and last spectra of the series are straightforwardly visible. It must be noted that for all normalization procedures under investigation the location of falsified bins is irrelevant.

3.2 Spectra from a Metabonomic Study for Normalization

Figure 6:
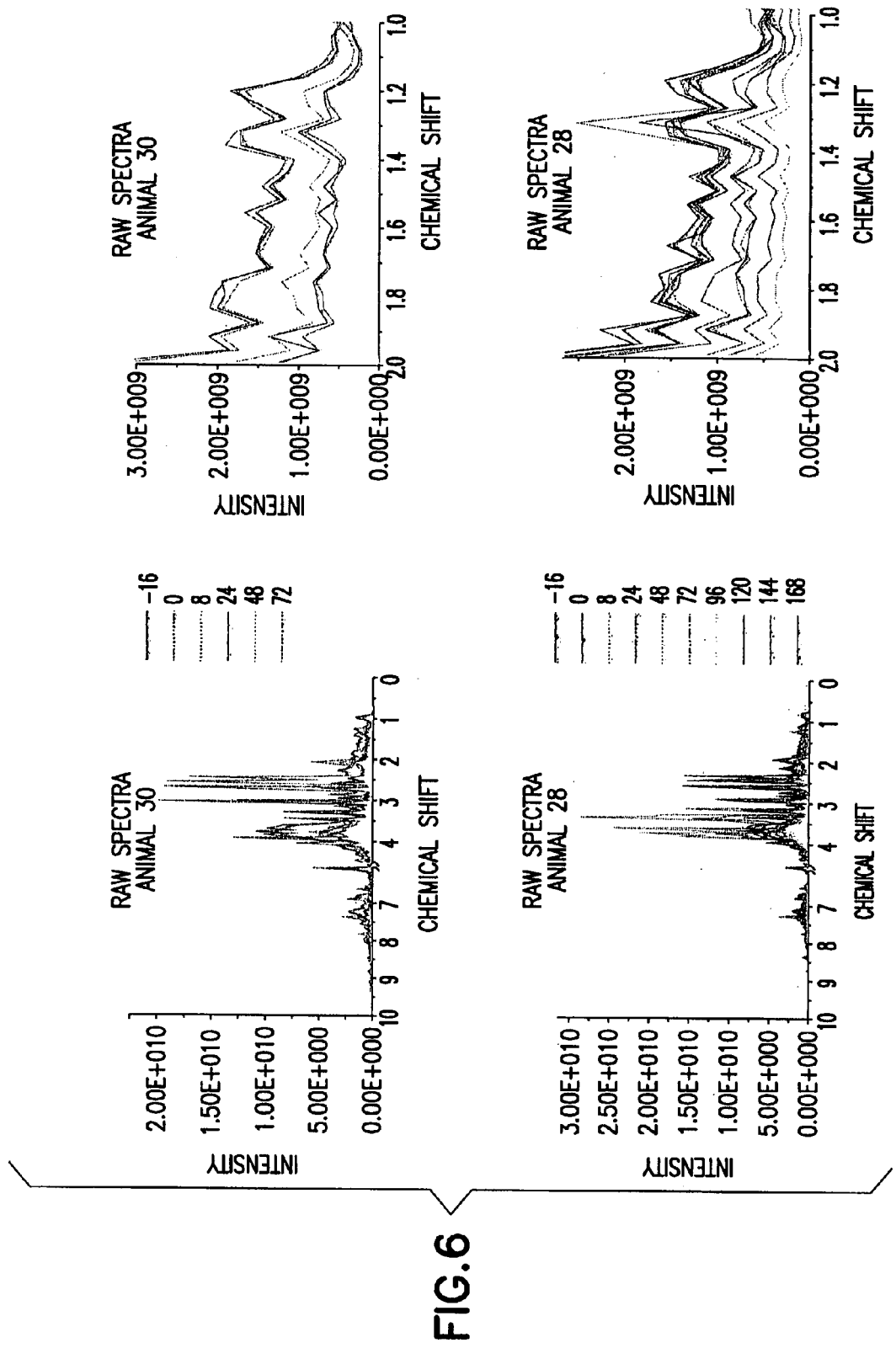
FIG. 6: shows raw spectra of two animals (animals no. 30 and no. 28) at different time points (−16$h$ to 72$h$ and −16$h$ to 168$h$ respectively) with zoomed regions shown on the right hand side.

The spectra of a real metabonomics study in which cyclosporin was administered to animals were used to test various normalization procedures with experimental data. The animal study, the measurements and the processing were performed according to the COMET protocol described elsewhere (Lindon J C, Nicholson J K, Holmes E, Antti H, Bollard M E, Keun H, Beckonert O, Ebbels T M, Reily M D, Robertson D, Stevens G J, Luke P, Breau A P, Cantor G H, Bible R H, Niederhauser U, Senn H, Schlotterbeck G, Sidelmann U G, Laursen S M, Tymiak A, Car B D, Lehman-McKeeman L, Cole J M, Loukaci A, Thomas C, Tox Appl Paramacology 187, 2003, 137-146). The data set contains 231 samples in total obtained by sampling 10 control animals, 10 low-dosed animals and 10 high-dosed animals at different time points. From this data set, 18 samples were removed that had been detected as outliers due to technical issues. Binning and exclusion of spectral regions was performed as described in section 3.1. The non-normalized spectra of all time points of two high-dosed animals and a zoomed part are shown in FIG. 6.

3.3 Control Samples for Normalization

To validate the performance of the different normalization procedures not only under difficult conditions of strong metabonomic responses but also under normal conditions, a collection of NMR spectra of non-dosed rats was set up. Thereby, 4023 samples out of 4521 sample from control animals and pre-dosed samples were selected on the basis of least extreme variations. This collection of samples represents normal variations of metabonomic profiles of rats.

As all animals had not been dosed, the creatinine level of the samples was not influenced by metabonomic changes and thus represents a good measure for the overall concentration of samples. Hence, the performance of the normalization procedures can be compared on the basis of variations of the creatinine level of normalized samples. Hereby, the creatinine level was determined by the integral of the spectrum between 4.02 and 4.10 ppm to account for shifts of the creatinine peak due to variations of the pH.

3.4 Studies for Outlier Identification

For the identification of outliers, two studies were used. The first study corresponds to the cyclosporin study described in section 3.2, but the outliers identified manually were now included (in contrast to section 3.2). The second metabonomic study used rosiglitazone as administered compound and contains 80 samples, wherein 45 spectra originate from dosed animals and 35 spectra originate from non-dosed animals. Measurements and data processing were performed according to the COMET protocol (Lindon J C, et al.; loc. cit.). Again, outliers identified manually were not removed. The criteria for judging an overall quality of a study (see section 2.5) were applied to an additional, third study containing 60 samples (30 samples from dosed animals and 30 samples from non-dosed animals). The first measurement of this study was faced with problems concerning the suppression of water resonances resulting in poor automatic baseline correction and phasing. The data of this study were also manually baseline corrected and phased. In addition, the samples of this study were measured again using an optimized pulse sequence (Bax pulse) resulting in the best visual quality of spectra.

4. Results

The results are presented in following order. First, the integral normalization, the vector length normalization and the quotient normalization are compared using the simulated data sets. Then the comparison is made for the spectra of the metabonomics study. Finally, the possibility of using the quotient normalization for the detection of outliers is demonstrated using several metabonomics studies.

4.1 Normalization Procedures—Simulations

For the results of the simulated data sets (see section 3.1 for details), the quotients of the intensity of bin 0.4 ppm of the modified spectra and the golden spectra were calculated. This peak was modified artificially only according to unspecific changes of concentrations. Thus, by construction of this reference amplitude a quotient of 1 means optimal recovery of the relative peak intensity and with it an optimal normalization of the spectra by the corresponding normalization procedure.

4.1.1 Performance of Various Normalization Procedures

Figure 7:
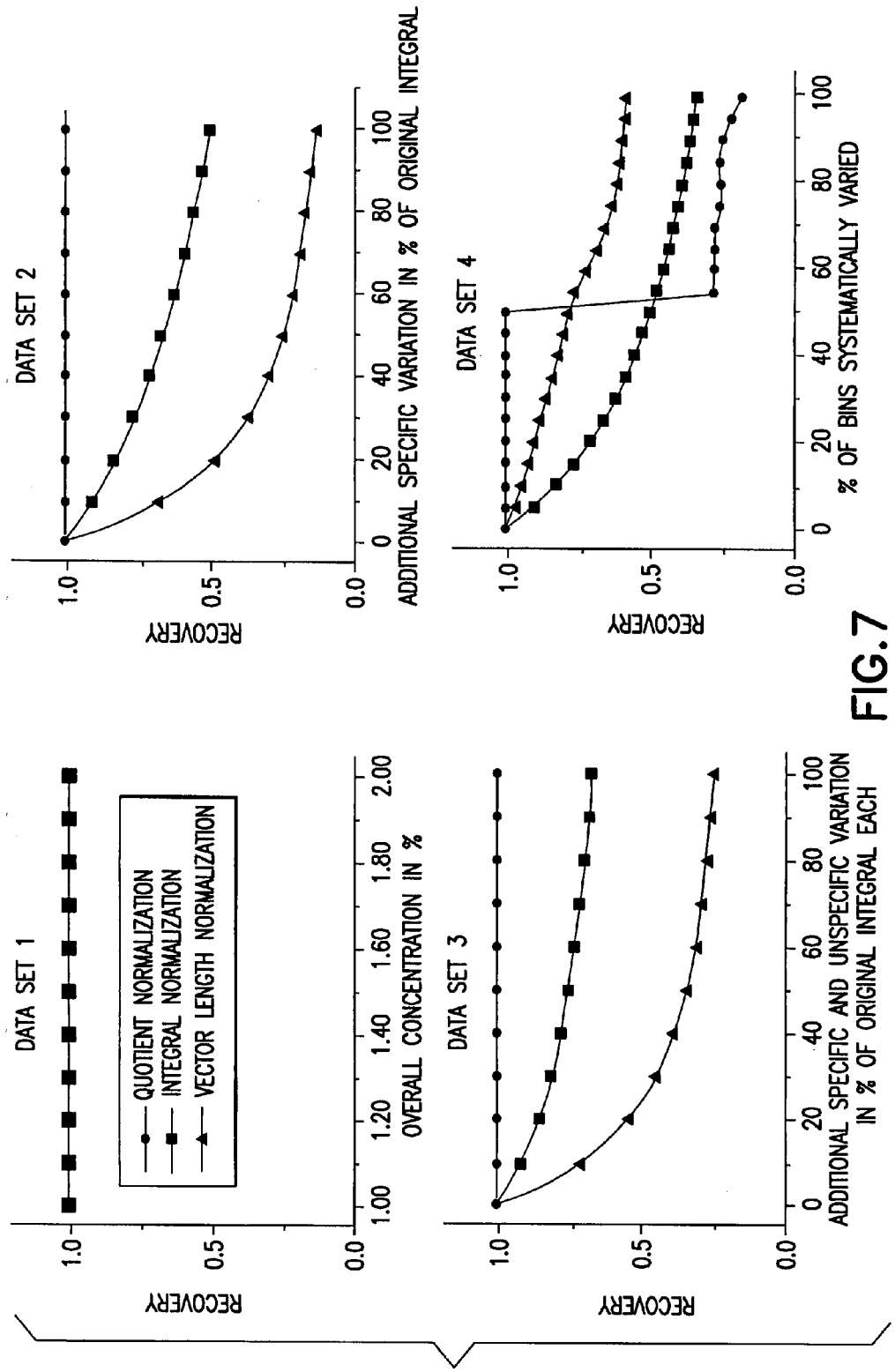
FIG. 7: shows the recovery achieved by different normalization procedures for the four data sets of FIG. 5; a recovery rate of 1 means that the normalization procedure rescales analytes with the same relative concentration in different samples to the same normalized concentration.

In this section, integral normalization and vector length normalization are compared with quotient normalization. For quotient normalization the golden spectrum was used as reference spectrum. Systematic variations of the reference spectrum are discussed later. In FIG. 7, the results of the three normalization procedures for the four data sets are shown. For data set 1, which only contains unspecific variations of the total concentrations, all three methods show an optimal normalization. The recovery rate of 1 means that the peaks and the analytes that only vary with total concentration (like dilution of samples) are normalized to the same constant concentration. As expected, all three procedures are capable of adequately normalizing spectra of an ideal series of dilution.

The second data set, which contains only specific changes of one single signal and no dilution, shows the three procedures to perform rather differently. The normalization to vector length is highly sensitive to changes of the single peak. Thereby, the increase of the length of the concentration vector due to the increase of a single bin of the spectrum is dramatic as the length is calculated using quadratic terms. The rescaling of the vector length is equally distributed over all bins, which results in an underestimation of the unchanged bins. For integral normalization, the deviations from ideal performance are less dramatic, as the effect of an increased intensity of one bin is distributed equally but without quadratic terms over all bins. For example, spectrum 10 contains additional 100% of the total intensity in one single bin, which upon integral normalization is distributed over all bins, thus resulting in a downscaling of all bins by a factor of 2. On the other hand, quotient normalization is not influenced by changes of a single bin and thus yields the optimal normalization for all spectra.

The third data set, which contains a combined variation of the first and second data set, shows rather similar results as the second data set. Variation of a single bin strongly influences the normalizations to vector length and to constant integral.

The fourth data set simulates combined changes of several bins. For the first spectrum, the intensity of 10 bins (out of 201) is increased (1% of total integral per bin), for the second spectrum the intensity of 20 bins is increased, and so on. For this case, the vector length normalization shows a better performance than the integral normalization, but both methods show a deviation from optimal normalization already for the first spectrum. On the other hand, quotient normalization shows an optimal normalization all the way to a systematical increase of intensity for 100 out of 201 bins. For spectra with systematical increases in even more bins, the performance dramatically drops. Yet, this case of systematical changes in the same direction for more than half of the bins is very unrealistic. For systematic variations of 5 to 25% of the bins, which can be considered as realistic scenarios, and even for systamtic variations of 30% to 50% of the bins, which are already very extreme scenarios, quotient normalization performs well.

4.1.2 Influence of Noise

The data analysis with the four datasets listed above was repeated twice, whereby artificial noise was added to the spectra. For the first repetition, uniform noise with a standard deviation of 0.6% of the average intensity per signal was added to each signal. This amount of noise was estimated as typical spectrometer noise from more than 4000 spectra in spectral regions where no biological variation exists. For the second repetition, the amount of noise was increased tenfold so as to approximate the typical biological noise of untreated animals. For both repetitions, all normalization procedures turned out not to be sensitive to noise. Indeed, the variations of the normalization factors are significantly lower than the variations per bin as the normalization procedures take all bins into account (smoothing effect). For example, the standard deviations for the normalization factors of data set 1 for 0.6% noise are between 0.04% and 0.1% and for 6% noise between 0.2% and 0.4%.

4.1.3 Influence of Reference Spectrum for Quotient Normalization

In contrast to vector length normalization and integral normalization, a reference spectrum is needed for quotient normalization. The influence of the reference spectrum on the performance of quotient normalization is investigated in this section. Besides of using the "golden spectrum" (1) as reference spectrum, the following reference spectra were also used:

(2) Median spectrum of all the spectra of the three times four simulated data sets that differed only by unspecific changes and by noise. The median spectrum is constructed by using the median for each signal bin out of all candidate spectra.

(3) Median spectrum of all spectra that differed only by unspecific changes, by noise and by specific changes that are less or equal to 20% of the total integral.

(4) Median spectrum of all spectra that differed only by unspecific changes, by noise and by specific changes that are less or equal to 100% of the total integral.

(5) Median spectrum of all spectra (all three times four data sets).

(6) A spectrum with a constant value of 1 in each bin.

Figure 8:
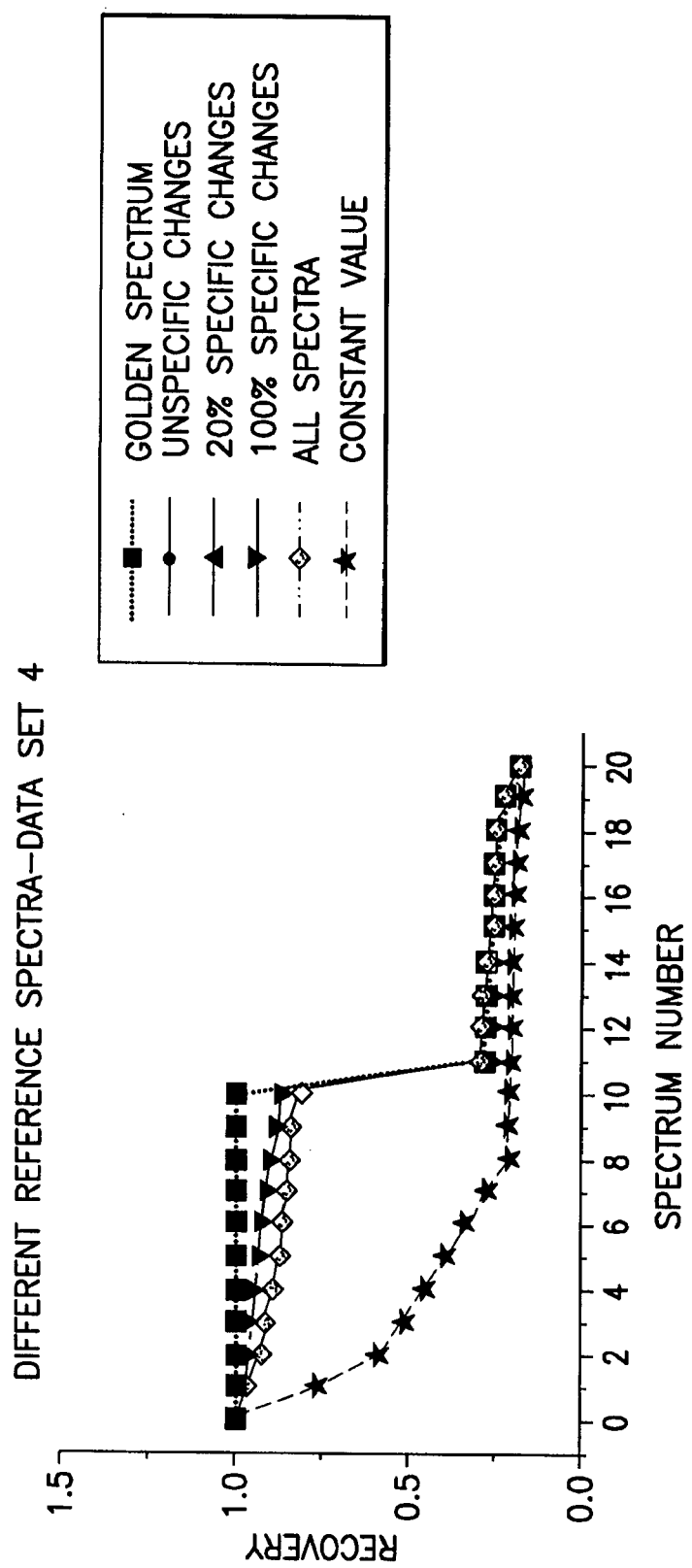
FIG. 8: shows the results for quotient normalization using different reference spectra.

For the above mentioned six different reference spectra, quotient normalizations of the four noise-free data sets described before were performed. For the first three data sets, no significant differences between the reference spectra can be observed. For the fourth data set, clear differences can be seen in FIG. 8. Using a constant value as reference spectrum shows a very bad performance. This finding is self-evident as the distribution of spectral quotients between the spectrum and the reference spectrum corresponds to the distribution of the spectrum itself and consequently is flat and broad. Therefore, an increase of several peaks will significantly shift the median. It is seen that the most stable normalization is obtained if the reference spectrum corresponds as well as possible to a representative spectrum without specific changes (unspecific changes are allowed). It is also seen that specific changes of up to 20% of the total intensity do not significantly influence the normalization, whereas the normalization using spectra with up to 100% specific changes of the integrated intensity is less stable. As the complete data set 6 contains an unrealistically high number of spectra with exceedingly high specific changes of many bins, the simulation with all data shown in FIG. 8 is clearly an exaggeration of the influence of the reference spectrum. Nevertheless, the simulation demonstrates that the best way of normalizing a study is using a spectrum representing data of non-dosed animals such as control animals and/or pre-dosed time points as reference spectrum. A feasible way of calculating a representative spectrum is to use the average or median of a number of control spectra or pre-dosed spectra respectively. The advantage of calculating the median instead of an average is a higher tolerance for outliers among the spectra. This is often encountered in metabonomic studies.

The purpose of the simulated data sets was to test the different normalization procedures under realistic, extreme and to some extent unrealistic conditions. The specific changes of signals were all performed in only one direction (increase of signals), as this is more demanding for normalization procedures: if different signals specifically change into different directions, the changes balance each other in respect to normalization procedures. For example, if 20 signals increase by 10 intensity units and 15 signals decrease by 10 intensity units, normalization procedures are effected only by changes of 5 signals. Thus, for realistic conditions the simulations using data set 4 should only be regarded for the first few spectra and not for all spectra.

When looking at the different simulations, it is very clear that quotient normalization outperforms both common normalization procedures for all different realistic and extreme conditions. Especially when single bins are changed extremely, which can happen in metabonomic studies, the quotient normalization still finds the optimal normalization factor, whereas both other normalization procedure distribute the effect of the excess intensity of single bins over all bins. Thereby an artificial negative correlation of all other bins with the factor influencing only single bins is introduced.

Additionally, it was shown in this simulation that the best reference spectrum for quotient normalization is a spectrum that is most representative without specific changes. Thus, for metabonomic spectra the optimal reference spectrum should be calculated on the basis of control animals or spectra of animals at pre-dosed time-points (for example calculated as median spectrum).

4.2 Normalization Procedures—Cyclosporin Study

In this section, the performance of the three normalization procedures is compared using data of a complete metabonomic study described in section 3.2 in detail. By visual inspection it was found that all signals between chemical shifts of 1.44 ppm and 1.84 ppm are very constant for different animals and different time points. These signals are not influenced by specific metabonomic changes in this study and are only subject to differences of the urine concentration. Thus, the relative standard deviations of the integrals of this part of the spectra between the different samples are used as quality criterion for the normalization procedure. This part of the spectra normalized using different methods is plotted for the two high-dosed animals 28 and 30 in FIG. 9. Animal 28 excreted extreme amounts of glucose at time points 48$h$ and 72$h$, whereas animal 30 shows typical metabonomic responses at all time points. For comparison, the complete non-normalized spectra of the two animals are shown in FIG. 6.

Finally, all samples of the study were used to investigate the correlation between the normalization factors of the different procedures and the concentrations of creatinine determined as integral between 4.02 and 4.10 ppm.

Figure 9:
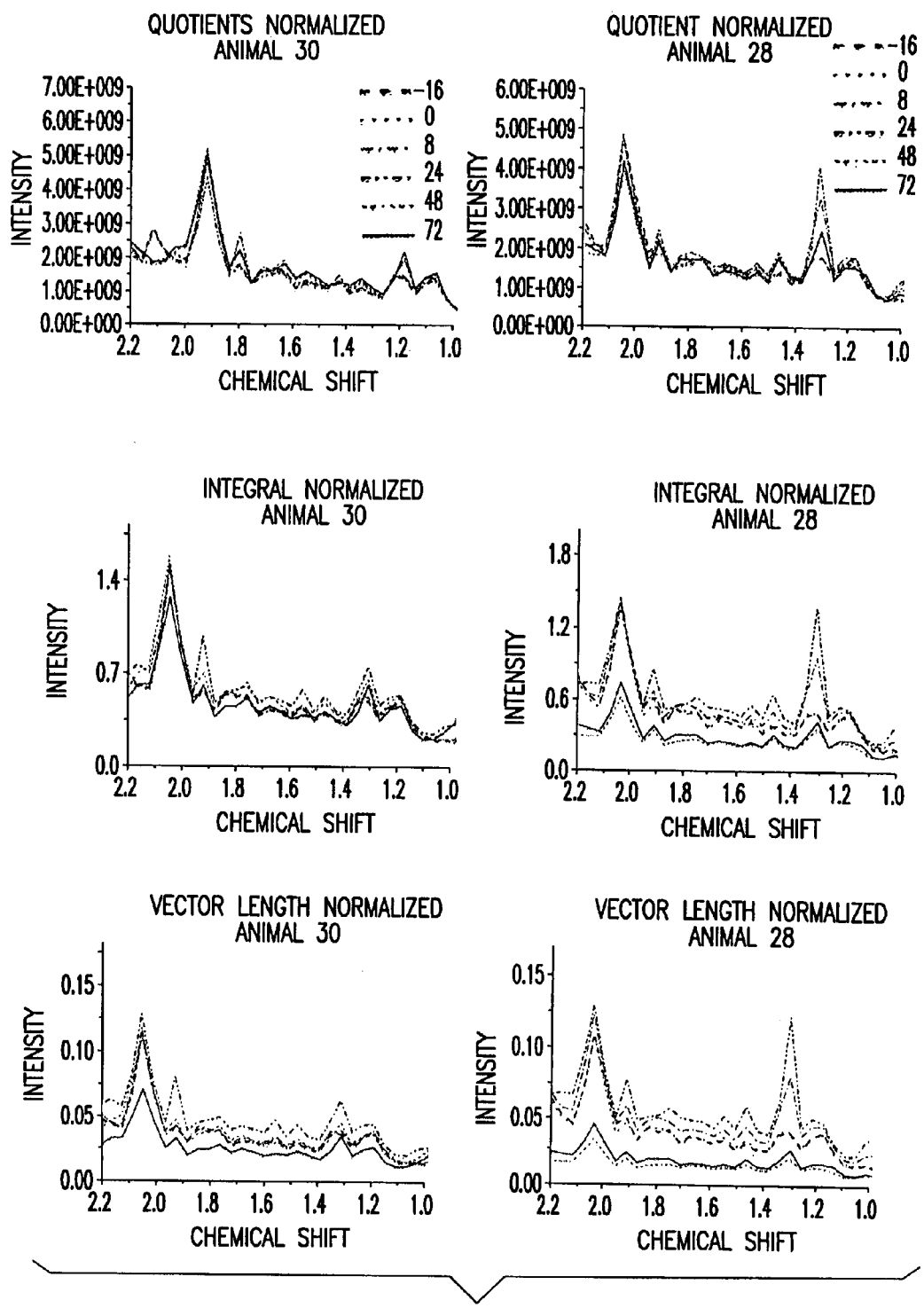
FIG. 9: shows, for animals no. 30 and 28, at different time points, a spectral region containing mainly signals that do not vary due to metabonomic responses (1.44-1.84 ppm); the top row shows quotient normalized spectra, the middle row shows vector length normalized spectra and the bottom row shows vector length normalized spectra.

For integral normalization, the spectra of animal 28 and 30 are shown in the middle row of FIG. 9. It is obvious that the spectra of animal 30 show rather congruent signals between 1.44 ppm and 1.84 ppm, whereas for animal 28 the spectra of the time points 48$h$ and 72$h$ are too low. The spectra of these time points show very high glucose peaks which suppress the rest of the spectrum due to the constraint of a total integral. The integrals between 1.44 ppm and 1.84 ppm of all integral normalized samples of the study show a relative standard deviation of 10.3%. The linear regression of the normalization factor versus the creatinine peak shows a correlation coefficient of 0.87.

The plots of the vector length normalization (FIG. 9, bottom row) show a poor normalization. Several spectra of both animals show too low or too high signals between 1.44 and 1.84 with the two Glucose samples (animal 28, 48$h$ and 72$h$) most extremely outlying. The signals within this region differ among all samples, as seen by a relative standard deviation of 15.0%. Also the correlation with creatine is poor ($r=0.62$).

Inspection of the top row of FIG. 9 reveals that quotient normalization is superior for the samples plotted here. The signals between 1.44 and 1.84 are very congruent for all samples. The low relative standard deviation of 4.5% for the signals of all samples in this region and the excellent correlation with the creatinine peak ($r=0.99$) demonstrate that quotient normalization is the most consistent normalization for the complete study.

4.3 Normalization Procedures—Normal Samples

An interesting issue is validating the performance of different normalization procedures not only under difficult conditions but also under "normal conditions" of control animals and pre-dosed samples. The selected 4023 non-dosed samples (see section 3.3 for details) do not contain strong metabonomic responses or drug related compounds. Therefore, it is expected that all three normalization procedures should show a similar performance. As the non-dosed animals should have a rather constant relative creatinine level, the performance of the three normalization methods is assessed here by the relative standard deviation of the creatinine peak.

The results are rather remarkable: The vector length normalization has an unacceptably high relative standard deviation of the creatinine peak of 12.2%, whereas the integral normalization has a low relative standard deviation of 7.6% and the quotient normalization has the best performance with 6.7%. This means that even when looking at control animals, specific variations due to metabonomic fluxes are so high that significant differences between normalization procedures exist, whereby quotient normalization shows the best performance again.

4.4 Outlier Identification

Figure 10:
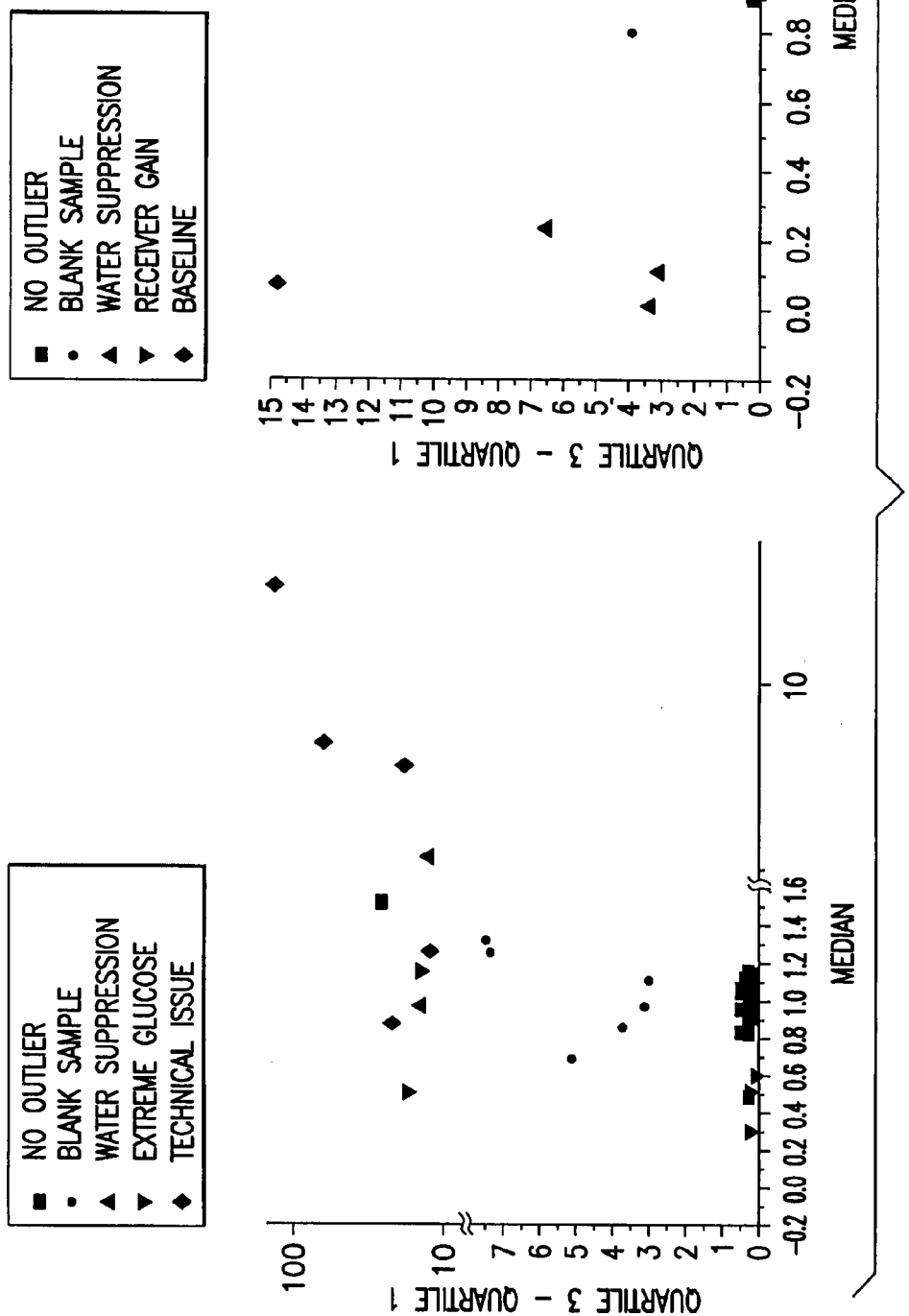
FIG. 10: shows interquartile differences d versus medians m for graphical detection of outliers in a cyclosporin study (left side) and in a rosiglitazone study (right side)
Figure 11:
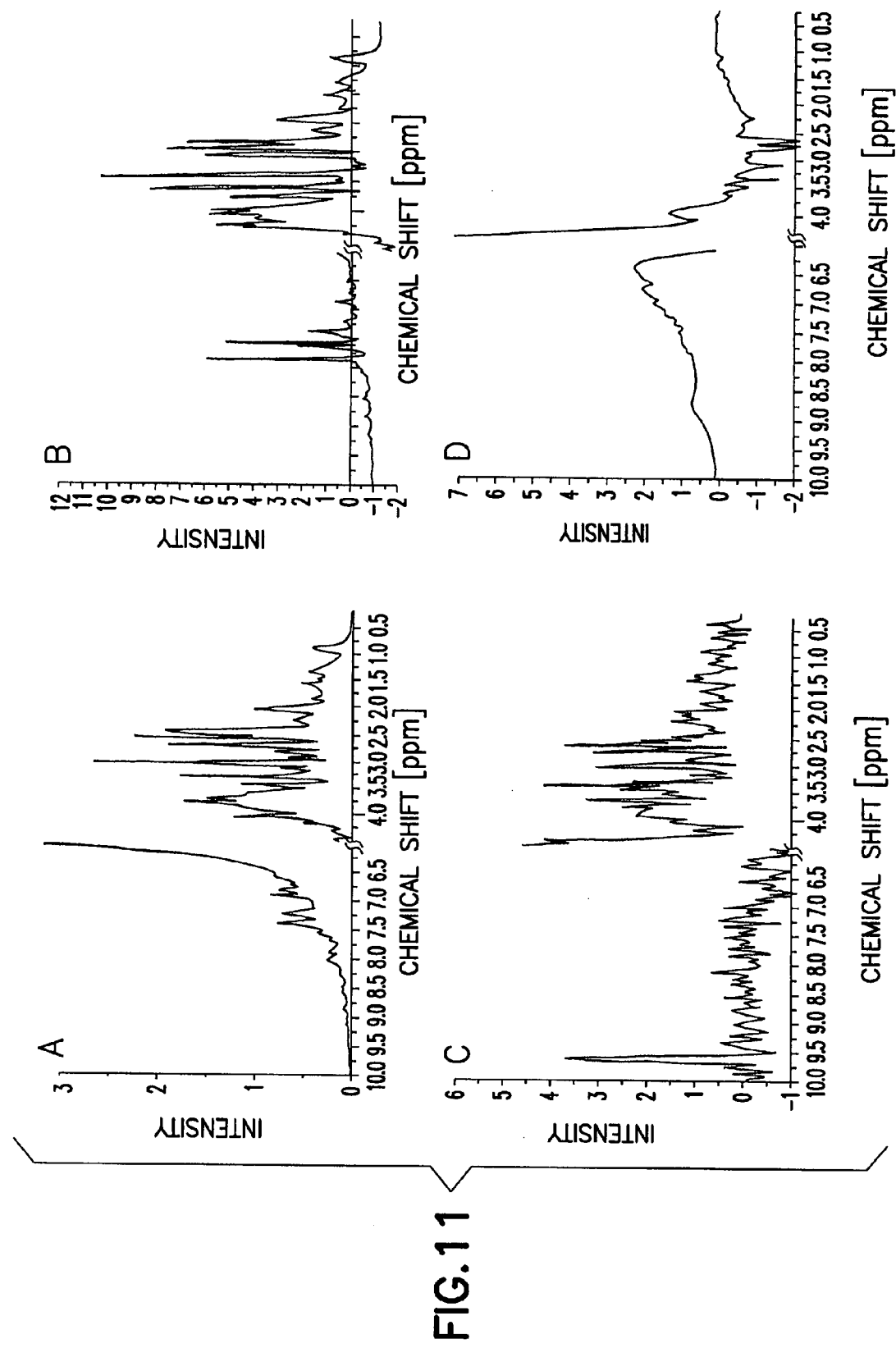
FIG. 11: shows some of the spectra identified as outliers in the right side plot of FIG. 10: (A) poor suppression of water resonances; (B) negative baseline; (C) blank sample and (D) spectrum taken with technical problems such as air bubbles.

The cyclosporin study including the outliers detected by visual inspection of the spectra was normalized by the quotient normalization procedure (see section 3.4 for details about the data sets). For the automatic identification of outliers, the interquartile differences between the third and first quartiles d of the spectral quotients were calculated in addition to the medians m of quotients for each sample. In the left panel of FIG. 10, d is plotted versus m for all samples of the study. The outliers found by visual inspection of the spectra are shown as dots, triangles and diamonds. It is obvious that all non-outlying samples cluster at very low values of d and at a median of about 1. Samples with extreme metabonomic responses, in this case extreme amounts of glucose, are located at low values of d and at low values of m. Outliers due to technical issues, blank samples and samples with a poor suppression of the water resonances are all located at high values of d (higher than 3). This means that a simple threshold of d>1 detects all outliers due to non-metabonomic related issues. Also, the extreme glucose samples can be detected as extreme metabonomic responses with simple thresholds of d<1 and m<0.8. The quality chart of a second study (see section 3.4) is shown in the right panel of FIG. 10. Again, a simple threshold of d>1 detects all outliers that had previously been identified by visual inspection of all the spectra. Some of the outlying spectra due to typical issues are shown in FIG. 11.

Figure 12:
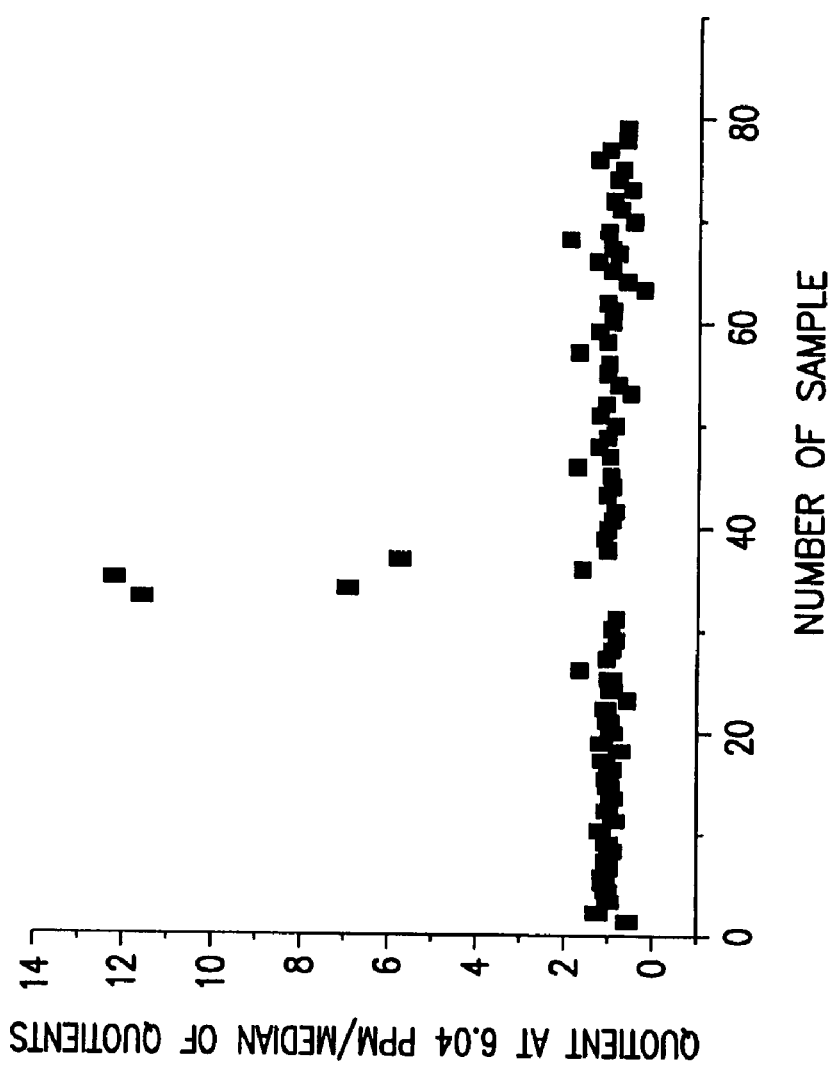
FIG. 12: shows, for the signal bin corresponding to a chemical shift of 6.04 ppm, as a plot versus sample number, the spectral quotient obtained by dividing the sample signal by the median of all quotients; values strongly deviating from 1 indicate problems with the suppression of water resonances in the corresponding sample.

In FIG. 12 it is demonstrated for the rosiglitazone study how quotient normalization can be used for detecting specific problems. In this example the quality of the suppression of water resonances is monitored. First, a quotient normalization for the study was performed. Then, the spectral quotients of the spectrum at 6.04 ppm divided by the median of all quotients was calculated. If the corresponding value strongly deviates from 1, the spectrum is significantly different from the reference next to the water resonances. It is obvious that four samples have a poor water suppression. These four samples have also been manually identified and are shown as triangles ▲ in the right panel of FIG. 10.

TABLE 1

Different quality features for three data sets. Lower values of the quality features represent more similar shapes of the spectra throughout the complete study.

| Data set | md | dd |
|---|---|---|
| First measurement | 0.38 | 0.60 |
| Manual reprocessing | 0.33 | 0.38 |
| Second measurement | 0.27 | 0.29 |

A further application of quotient normalization is shown in Table 1 for a third data set (see section 3.4). Therein, medians of inter-quartile differences md and the differences of inter quartile differences dd (see section 2.5 for details) are shown. The first measurement had a poor water suppression for several samples, which negatively influenced the automatic phasing and baseline correction. A manual baseline correction and phasing could improve the visual quality of these samples. Nevertheless, a second measurement of the samples with optimized pulse sequences significantly improved the water suppression and the quality of spectra (as confirmed by visual inspection). From Table 1 it is obvious that all three outlier criteria agree with the visual impression of the quality of the spectra. Thereby md expresses an average inhomogenity within spectra. As only some spectra are affected by a poor water suppression, md decreases only moderately. On the other side, dd, which describes the variance of this inhomogenity between different spectra, decreases dramatically, as the re-processing and re-measurement of the samples mainly improved samples with a bad water suppression. Both quality features allow to assess the homogeneity within spectra and between spectra without the need of inspecting spectra.

The invention claimed is:

1. A method of automated discarding of outliers in a set of spectra obtained by spectroscopy, the spectroscopy yielding spectra, such as NMR spectra, containing signals or peaks whose intensities or areas are proportional to component concentrations, comprising the steps of:
   a) selecting a principal spectral range;
   b) recording a plurality of principal spectra in said principal spectral range;
   c) obtaining a reference principal spectrum in said principal spectral range;
   d) carrying out, for each one of said principal spectra, a bin-wise division of the principal spectrum by said reference principal spectrum to obtain a corresponding set of spectral quotients;
   e) calculating, for at least one of said principal spectra, an associated set of statistical measures derived from the corresponding set of spectral quotients, said set of statistical measures corresponding to a principal spectrum comprising the median of its spectral quotients and an interquartile difference obtained by subtracting the first quartile of its spectral quotients from the third quartile of its spectral quotients;
   f) carrying out, for at least one of said sets of statistical measures, an outlier detection test to determine whether the principal spectrum associated therewith is an outlier; and
   g) discarding said principal spectrum if it has been determined to be an outlier.

2. The method according to claim 1, wherein said outlier detection test comprises determining whether said interquartile difference exceeds a predefined threshold width.

3. The method according to claim 1, wherein said threshold width is determined from the distribution of said interquartile differences taken over the entire set of principal spectra.

4. The method according to claim 3, wherein said threshold quotient deviation is determined from the distribution of said median of spectral quotients taken over the entire set of principal spectra.

5. The method according to claim 1, wherein said outlier detection test comprises determining whether said median of spectral quotients differs from a constant by more than a predefined threshold quotient deviation.

6. The method according to claim 1, wherein said set of statistical measures comprises: a) the median of the complete set of said interquartile differences; and b) the interquartile difference of the complete set of said interquartile differences.

7. The method according to claim 6, wherein each one of said principal or auxiliary spectra is subjected to a normalization procedure before carrying out said bin-wise division.

8. The method according to claim 1, wherein step 1e) is carried out for each one of said principal spectra so as to obtain a complete set of statistical measures from which is derived a set of global statistical measures, and wherein said outlier detection test is carried out for said set of global statistical measures.

9. A method of automated discarding of outliers in a set of spectra obtained by spectroscopy, the spectroscopy yielding spectra, such as NMR spectra, containing signals or peaks whose intensities or areas are proportional to component concentrations, comprising the steps of:
  a) selecting a principal spectral range;
  b) recording a plurality of principal spectra in said principal spectral range;
  c) obtaining a reference principal spectrum in said principal spectral range;
  d) carrying out, for each one of said principal spectra, a bin-wise division of the principal spectrum by said reference principal spectrum to obtain a corresponding set of spectral quotients;
  e) calculating, for at least one of said principal spectra, an associated set of statistical measures derived from the corresponding set of spectral quotients;
  f) carrying out, for at least one of said sets of statistical measures, an outlier detection test to determine whether the principal spectrum associated therewith is an outlier;
  g) discarding said principal spectrum if it has been determined to be an outlier;
  h) selecting an auxiliary spectral range that does not overlap with said principal spectral range,
  i) recording, with each one of said principal spectra in said principal spectral range, an associated auxiliary spectrum in said auxiliary spectral range;
  j) obtaining a reference auxiliary spectrum in said auxiliary spectral range;
  k) carrying out, for each one of said auxiliary spectra, a bin-wise division of the auxiliary spectrum by said reference auxiliary spectrum to obtain a corresponding set of auxiliary spectral quotients; and
  l) calculating, for each one of said auxiliary spectra, an associated set of statistical measures derived from the corresponding set of auxiliary spectral quotients; wherein said outlier detection test comprises comparing statistical measures of a principal spectrum and of an associated auxiliary spectrum.

10. The method according to claim 9, wherein step 7e) is carried out for each one of said principal spectra so as to obtain a complete set of statistical measures from which is derived a set of global statistical measures, and wherein said outlier detection test is carried out for said set of global statistical measures.

11. The method according to claim 10, wherein said set of global statistical measures comprises: the median of the complete set of said interquartile differences; and the interquartile difference of the complete set of said interquartile differences.

12. The method according to claim 9, wherein each one of said principal or auxiliary spectra is subjected to a normalization procedure before carrying out said bin-wise division.

13. The method according to claim 12, wherein said normalization procedure for any one of said principal or auxiliary spectra comprises the steps of: applying to said spectrum a pre-processing to obtain a pre-processed spectrum; calculating an integrated intensity of said pre-processed spectrum; and multiplying said pre-processed spectrum by a normalization factor that is proportional to the inverse of said integrated intensity.

14. The method according to claim 13, wherein said reference principal or auxiliary spectrum is obtained as the median of a plurality of blank or control spectra recorded in the corresponding principal or auxiliary spectral range, respectively.

15. The method according to claim 13, wherein said reference principal or auxiliary spectrum is obtained from a subset of said principal or auxiliary spectra.

16. The method according to claim 9, wherein said reference principal or auxiliary spectrum is obtained as the median of a plurality of blank or control spectra recorded in the corresponding principal or auxiliary spectral range, respectively.

17. The method according to claim 9, wherein said reference principal or auxiliary spectrum is obtained from a subset of said principal or auxiliary spectra.

18. The method according to claim 9, wherein the set of statistical measures corresponding to a principal spectrum comprises the median of its spectral quotients and an interquartile difference obtained by subtracting the first quartile of its spectral quotients from the third quartile of its spectral quotients.

19. The method according to claim 9, wherein said set of global statistical measures comprises the median of the complete set of said interquartile differences, and the interquartile difference of the complete set of said interquartile differences.

* * * * *